United States Patent
Berlin

(10) Patent No.: US 8,029,996 B2
(45) Date of Patent: Oct. 4, 2011

(54) METHOD FOR THE DETERMINATION OF CYSTOSINE METHYLATION IN CPG ISLANDS

(75) Inventor: Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 585 days.

(21) Appl. No.: 10/491,743

(22) PCT Filed: Oct. 4, 2002

(86) PCT No.: PCT/DE02/03845
§ 371 (c)(1), (2), (4) Date: Oct. 7, 2004

(87) PCT Pub. No.: WO03/031649
PCT Pub. Date: Apr. 17, 2003

(65) Prior Publication Data
US 2005/0053937 A1 Mar. 10, 2005

(30) Foreign Application Priority Data
Oct. 5, 2001 (DE) ................................ 101 51 055

(51) Int. Cl.
*C07H 21/04* (2006.01)
*C12Q 1/68* (2006.01)
(52) U.S. Cl. ...... 435/6.1; 435/91.1; 435/91.2; 536/23.1; 536/24.3
(58) Field of Classification Search .................. None
See application file for complete search history.

(56) References Cited

U.S. PATENT DOCUMENTS
6,613,509 B1 * 9/2003 Chen .................................. 435/6
7,179,594 B1 * 2/2007 Berlin ............................... 435/6

FOREIGN PATENT DOCUMENTS
DE 199 51 189 A 5/2001
DE 100 50 942 A 4/2002
(Continued)

OTHER PUBLICATIONS
Maekawa et al. (Clin. Chem, Lab. Med. vol. 39, pp. 121-128, 2001).*
(Continued)

*Primary Examiner* — Jeanine A Goldberg
(74) *Attorney, Agent, or Firm* — Kriegsman & Kriegsman

(57) ABSTRACT

A method for the detection of cytosine methylation in DNA samples is described. First, DNA is extracted from a sample and bound to a surface. In the second step, a genomic DNA sample is preferably treated with a bisulfite (=disulfite, hydrogen sulfite), such that all unmethylated cytosine bases are converted to uracil, while the 5-methylcytosine bases remain unchanged. In the third step of the method, one or more oligonucleotides is (are) hybridized to the treated DNA as primers. In the fourth step of the method, the hybridized primer(s) is or are elongated in a polymerase reaction. Here, labeled guanine nucleotides are preferably utilized which are essentially incorporated only if cytosine bases were still present in the treated DNA. Consequently, the extent of incorporation of guanine bases and thus also the number of incorporated labels is proportional to the methylation in the DNA sample under investigation. In the fifth step of the method, the labeled nucleotides that were not incorporated in the polymerase reaction are removed. In the sixth step of the method, the number of labels in the fragment generated by the primer extension is approximately determined by directly or indirectly measuring signal intensities emitted by these labels.

17 Claims, 1 Drawing Sheet

FOREIGN PATENT DOCUMENTS

| | | |
|---|---|---|
| WO | WO 97/46705 A | 12/1997 |
| WO | WO 99/28498 A | 6/1999 |
| WO | WO 01/42493 A | 6/2001 |
| WO | WO 01/62064 A | 8/2001 |

OTHER PUBLICATIONS

Gonzalgo et al., "Rapid quant. of methylation diff. at specific sites using meth.-sensitive single nucl. primer ext. (Ms-SNuPE)," Nucleic Acids Research, 25(12):2529-31 (1997).

Olek et al., "A modified and improved method for bisulphite based cytosine methylation analysis," Nucleic Acids Research, 24(24):5064-6 (1996).

Xiong et al., "COBRA: a sensitive and quantitative DNA methylation assay," Nucleic Acids Research, Nucleic Acids Research, 25(12):2532-4 (1997).

MEDLINE Abstract No. 11266571 for Erdogan et al., Nucleic Acids Research, 29(7):E36 (2001).

Herman et al., "Methylation-specific PCR: A novel PCR assay for methylation status of CpG islands," PNAS, 93:9821-6 (1996).

\* cited by examiner

METHOD FOR THE DETERMINATION OF CYSTOSINE METHYLATION IN CPG ISLANDS

The present invention concerns a method for the particularly sensitive detection of cytosine methylation in DNA samples.

The levels of observation that have been well studied in molecular biology according to developments in methods in recent years include the genes themselves, the transcription of these genes into RNA and the translation to proteins therefrom. During the course of development of an individual, which gene is turned on and how the activation and inhibition of certain genes in certain cells and tissues are controlled can be correlated with the extent and nature of the methylation of the genes or of the genome. In this regard, pathogenic states are also expressed by a modified methylation pattern of individual genes or of the genome.

5-Methylcytosine is the most frequent covalently modified base in the DNA of eukaryotic cells. For example, it plays a role in the regulation of transcription, in genetic imprinting and in tumorigenesis. The identification of 5-methylcytosine as a component of genetic information is thus of considerable interest. 5-Methylcytosine positions, however, cannot be identified by sequencing, since 5-methylcytosine has the same base-pairing behavior as cytosine. In addition, in the case of a PCR amplification, the epigenetic information which is borne by the 5-methylcytosines is completely lost.

A relatively new method that in the meantime has become the most widely used method for investigating DNA for 5-methylcytosine is based on the specific reaction of bisulfite with cytosine, which, after subsequent alkaline hydrolysis, is then converted to uracil, which corresponds in its base-pairing behavior to thymidine. In contrast, 5-methylcytosine is not modified under these conditions. Thus, the original DNA is converted so that methylcytosine, which originally cannot be distinguished from cytosine by its hybridization behavior, can now be detected by "standard" molecular biology techniques as the only remaining cytosine, for example, by amplification and hybridization or sequencing. All of these techniques are based on base pairing, which is now fully utilized. The prior art, which concerns sensitivity, is defined by a method that incorporates the DNA to be investigated in an agarose matrix, so that the diffusion and renaturation of the DNA is prevented (bisulfite reacts only on single-stranded DNA) and all precipitation and purification steps are replaced by rapid dialysis (Olek A, Oswald J, Walter J. A modified and improved method for bisulphite based cytosine methylation analysis. Nucleic Acids Res. 1996 Dec. 15; 24(24):5064-6). Individual cells can be investigated by this method, which illustrates the potential of the method. Of course, up until now, only individual regions of up to approximately 3000 base pairs long have been investigated; a global investigation of cells for thousands of possible methylation analyses is not possible. Of course, this method also cannot reliably analyze very small fragments of small quantities of sample. These are lost despite the protection from diffusion through the matrix.

An overview of other known possibilities for detecting 5-methylcytosines can be derived from the following review article: Rein T, DePamphilis M L, Zorbas H. Identifying 5-methylcytosine and related modifications in DNA genomes. Nucleic Acids Res. 1998 May 15; 26(10):2255-64.

The bisulfite technique has been previously applied only in research, with a few exceptions (e.g., Zeschnigk M, Lich C, Buiting K, Dörfler W, Horsthemke B. A single-tube PCR test for the diagnosis of Angelman and Prader-Willi syndrome based an allelic methylation differences at the SNRPN locus. Eur J Hum Genet. 1997 March-April; 5(2):94-8). However, short, specific segments of a known gene have always been amplified after a bisulfite treatment and either completely sequenced (Olek A, Walter J. The pre-implantation ontogeny of the H19 methylation imprint. Nat Genet. 1997 November; 17(3):275-6) or individual cytosine positions have been detected by a "primer extension reaction" (Gonzalgo M L, Jones P A. Rapid quantitation of methylation differences at specific sites using methylation-sensitive single nucleotide primer extension (Ms-SNuPE). Nucleic Acids Res. 1997 Jun. 15; 25(12):2529-31, WO-Patent 9500669) or an enzyme cleavage (Xiong Z, Laird P W COBRA: a sensitive and quantitative DNA methylation assay. Nucleic Acids Res. 1997 Jun. 15; 25(12):2532-4). Detection has also been described by hybridization (Olek et al., WO 99/28498).

Urea improves the efficiency of bisulfite treatment prior to the sequencing of 5-methylcytosine in genomic DNA (Paulin R, Grigg G W, Davey M W, Piper A A. Urea improves efficiency of bisulphite-mediated sequencing of 5'-methylcytosine in genomic DNA. Nucleic Acids Res. 1998 Nov. 1; 26(21):5009-10).

Other publications which are concerned with the application of the bisulfite technique for the detection of methylation in the case of individual genes are:

Grigg G, Clark S. Sequencing 5-methylcytosine residues in genomic DNA. Bioessays. 1994 June; 16(6):431-6, 431; Zeschnigk M, Schmitz B, Dittrich B, Buiting K, Horsthemke B, Dörfler W. Imprinted segments in the human genome: different DNA methylation patterns in the Prader-Willi/Angelman syndrome region as determined by the genomic sequencing method. Hum Mol. Genet. 1997 March; 6(3): 387-95; Feil R, Charlton J, Bird A P, Walter J, Reik W. Methylation analysis on individual chromosomes: improved protocol for bisulphite genomic sequencing. Nucleic Acids Res. 1994 Feb. 25; 22(4):695-6; Martin V, Ribieras S, Song-Wang X, Rio M C, Dante R. Genomic sequencing indicates a correlation between DNA hypomethylation in the 5' region of the pS2 gene and in its expression in human breast cancer cell lines. Gene. 1995 May 19; 157(1-2):261-4; WO 97-46705, WO 95-15373 and WO-45560.

Another known method is the so-called methylation-sensitive PCR (Herman J G, Graff J R, Myohanen S, Nelkin B D, Baylin S B (1996), Methylation-specific PCR: a novel PCR assay for methylation status of CpG islands. Proc Natl Acad Sci USA. September 3; 93(18):9821-6). For this method, primers are used which hybridize either only to a sequence that forms by the bisulfite treatment of a DNA which is unmethylated at the respective position, or, vice versa, primers which bind only to a nucleic acid which forms by the bisulfite treatment of a DNA methylated at the respective position. Amplified products can be produced accordingly with these primers, the detection of which in turn supplies indications of the presence of a methylated or unmethylated position in the sample to which the primers bind.

A newer method is also the detection of cytosine methylation by means of a Taqman PCR, which has become known as "methyl light" (WO 00/70090). It is possible with this method to detect the methylation state of individual positions or a few positions directly in the course of the PCR, so that a subsequent analysis of the products becomes superfluous.

An overview of the prior art in oligomer array production can be derived also from a special issue of Nature Genetics which appeared in January 1999 (Nature Genetics Supplement, Volume 21, January 1999), the literature cited therein and U.S. Pat. No. 5,994,065 on methods for the production of solid supports for target molecules such as oligonucleotides in the case of reduced nonspecific background signal.

Probes with multiple fluorescent labels have been used for scanning an immobilized DNA array. Particularly suitable for fluorescent labels is the simple introduction of Cy3 and Cy5 dyes at the 5'-OH of the respective probe. The fluorescence of the hybridized probes is detected, for example, by means of a confocal microscope. The dyes Cy3 and Cy5, among many others, are commercially available.

Matrix-assisted laser desorptions/ionization mass spectrometry (MALDI-TOF) is a very powerful development for the analysis of biomolecules (Karas M, Hillenkamp F. Laser desorption ionization of proteins with molecular masses exceeding 10,000 daltons. Anal Chem. 1988 Oct. 15; 60(20): 2299-301). An analyte is embedded in a light-absorbing matrix. The matrix is vaporized by a short laser pulse and the analyte molecule is transported unfragmented into the gaseous phase. The analyte is ionized by collisions with matrix molecules. An applied voltage accelerates the ions in a field-free flight tube. Ions are accelerated to varying degrees based on their different masses. Smaller ions reach the detector sooner than large ions.

MALDI-TOF spectroscopy is excellently suitable for the analysis of peptides and proteins. The analysis of nucleic acids is somewhat more difficult (Gut, I. G. and Beck, S. (1995), DNA and Matrix Assisted Laser Desorption Ionization Mass Spectrometry. Molecular Biology: Current Innovations and Future Trends 1: 147-157.) For nucleic acids, the sensitivity is approximately 100 times poorer than for peptides and decreases overproportionally with increasing fragment size. For nucleic acids, which have a backbone with a multiple negative charge, the ionization process through the matrix is basically inefficient. In MALDI-TOF spectroscopy, the choice of matrix plays an imminently important role. Several very powerful matrices, which produce a very fine crystallization, have been found for the desorption of peptides. In the meantime, several effective matrices have been developed for DNA, but the difference in sensitivity has not been reduced thereby. The difference in sensitivity can be reduced by modifying the DNA chemically in such a way that it resembles a peptide. Phosphorothioate nucleic acids, in which the usual phosphates of the backbone are substituted by thiophosphates, can be converted by simple alkylation chemistry into a charge-neutral DNA (Gut, I. G. and Beck, S. (1995), A procedure for selective DNA alkylation and detection by mass spectrometry. Nucleic Acids Res. 23: 1367-1373). The coupling of a "charge tag" to this modified DNA results in an increase in sensitivity by the same amount as is found for peptides. Another advantage of "charge tagging" is the increased stability of the analysis in the presence of impurities, which make the detection of unmodified substrates very difficult.

Genomic DNA is obtained from DNA of cells, tissue or other assay samples by standard methods. This standard methodology is found in references such as Fritsch and Maniatis, Molecular Cloning: A Laboratory Manual, 1989.

After the invention of PCR, numerous variants became known in the following few years, which refine this technique for the amplification of DNA. In particular, multiplexing of the PCR (multiplex PCR) should be mentioned here, in which more than 2 specific primers are used and thus a plurality of different, specific amplifications can be produced in one reaction vessel. Particularly interesting also is the so-called nested PCR, which is used among other things for the detection of particularly small DNA quantities. This type of PCR is comprised of two successive amplifications, wherein the primers of the second amplification lie within the first amplificate and are not identical with the primers of the first amplification. In this way, a particular specificity is achieved, since the primers of the second amplification only function if the intended fragment was produced in the first amplification. In contrast, the propagation of any possible byproducts of the first amplification is excluded in the second amplification as much as possible.

Accordingly, a great many methods for methylation analysis are prior art. The present invention, however, will provide a possibility for the analysis of the degree of methylation overall in a CpG island. Preferably, a polymerase reaction, which facilitates conducting the method, need not be conducted. It is essential within the framework of a methylation analysis in the field of clinical diagnosis that results of investigation can be made available as rapidly as possible and that the experimental expenditure is kept as small as possible. The method described here, which measures the extent of methylation overall in a CpG island, is particularly suitable for this purpose. In contrast to the methods for methylation analysis that have been previously described, the methyllation state of an individual or several individual CpG positions is thus not determined. In many cases, the latter can be a disadvantage, since entire promotor regions can be present comethylated, i.e., many sequential CpG positions possess the same methylation state.

The present invention takes advantage of the fact that this methylation state is assumed to be similar in numerous positions to be investigated, and a signal can be generated, which results from the sum of these individual positions. This makes possible a sensitivity which can be sufficient without conducting a PCR reaction.

The method also takes advantage of the fact that guanine bases in bisulfite-treated DNA on one strand will only be incorporated in a subsequent polymerase reaction if a methylated cytosine was present in the corresponding genomic DNA sample. If the sample DNA contains no methylations at the respective positions, then guanine is not incorporated in the polymerase reaction.

And vice versa, also if a counterstrand was produced in a PCR reaction relative to bisulfite-treated DNA (after bisulfite treatment, the DNA strands of the sample are no longer complementary as they were originally), then with this counterstrand as a template, a cytosine is incorporated in a subsequent polymerase reaction, only if originally a methylated cytosine was present in the corresponding genomic DNA sample.

It thus follows that guanines or cytosines will be incorporated only if a methylation was present in the genomic DNA sample. The extent of incorporation of guanines or cytosines (depending on the method each time; see above) is directly correlated with the extent of methylation in the investigated genomic DNA segment.

The method according to the invention thus consists of the following steps:
First, the genomic DNA is extracted from a sample and then preferably bound to a surface, this binding most preferably produced by hybridization to an immobilized oligonucleotide and in turn the genomic DNA is most preferably cleaved by restriction enzymes prior to the binding.

It is preferred according to the invention that the DNA samples are obtained from serum or other body fluids of an individual.

It is additionally preferred according to the invention, that the DNA samples are obtained from cell lines, blood, sputum, stool, urine, serum, cerebrospinal fluid, tissue embedded in paraffin, for example, tissue from intestine, kidney, brain, heart, prostate, lungs, eyes, breast or liver, histological slides and all possible combinations thereof.

The enzymatic step for the DNA is most preferably conducted with a restriction endonuclease or several different restriction enzymes. If several restriction endonucleases are used, then it depends on the respective buffers whether these are applied sequentially or simultaneously. The use of restriction enzymes according to the protocols supplied by the manufacturers is known to the person skilled in the art.

In the second step, a genomic DNA sample is preferably treated with a bisulfite (=disulfite, hydrogen sulfite), such that all unmethylated cytosine bases are converted to uracil, while the 5-methylcytosine bases remain unchanged. Most preferably, this occurs at the surface onto which the sample DNA was already bound in the first step. It is most particularly preferred according to the invention that the chemical treatment is conducted with a bisulfite (=disulfite, hydrogen sulfite). It is also preferred that the chemical treatment is conducted after embedding the DNA in agarose. It is also and additionally preferred that in the chemical treatment, a reagent that denatures the DNA duplex and/or a radical trap are present.

In the third step of the method, one or more oligonucleotides is/are hybridized as primers to the treated DNA.

In the fourth step of the method, the hybridized primer(s) is or are elongated in a polymerase reaction. Here, labeled guanine nucleotides are utilized which are essentially incorporated only if cytosine bases were still present in the treated DNA. Consequently, the extent of incorporation of guanine bases and thus also the number of incorporated labels is proportional to the methylation in the DNA sample under investigation. Most preferably, the polymerase reaction terminates at the position which was cleaved in the first step by the use of a restriction endonuclease.

In the fifth step of the method, the labeled nucleotides that were not incorporated in the polymerase reaction are removed. Most preferably this is done by simple washing steps in the case where the DNA is present bound to a surface.

In the sixth step of the method, the number of labels in the fragment generated by primer extension is approximately determined by directly or indirectly measuring the signal intensity emitted by these labels.

The methylation state of the DNA sample in the investigated fragment is concluded from the signal intensity.

Labels can be, for example, fluorescent labels, radionuclides, or removable mass labels, which are detected in a mass spectrometer. Labels such as peptides, which are detected indirectly by the binding of an antibody which is labeled in a different way, however, can also be used. Chemical labels are also conceivable, which can be made visible only by subsequent reaction with a marker molecule which is labeled in a different way and which can be, for example, a fluorescent dye. A great many possibilities for providing molecules with labels are familiar to the person skilled in the art. The possibilities listed here will thus be understood as examples, and other possibilities for labeling that are familiar to the person skilled in the art will be considered as a component of this invention.

In the above-named steps, the amplification of the treated DNA sample is dispensed with. The method is thus particularly applicable when the sample quantity is not limiting and the labels used can be detected with sufficient sensitivity. However, in the investigation of a CpG island, for example, according to the above-described method, since a plurality of labels will be incorporated in the polymerase reaction, if the CpG island was present methylated, a considerable increase in sensitivity will be achieved also by the type of method conducted.

If an increased sensitivity is required due to a very small amount of DNA, then the above-described method will be completed by a PCR reaction or another polymerase reaction, which is not just a linearly amplifying reaction and which will be conducted after treatment according to the second method step. Preferably the (chemically) treated DNA sample will be amplified with the use of preferably at least 2 primer oligonucleotides by means of a polymerase reaction, wherein preferably a heat-stable polymerase, nucleotides as well as a suitable reaction buffer, as are often supplied with the polymerase and known to the person skilled in the art, will be used.

It is also particularly preferred to conduct the amplifications of several different fragments with more than 2 different primers in one reaction vessel and thus to carry out the amplification steps as a multiplex PCR. It is generally particularly preferred to conduct the amplifications as a polymerase chain reaction.

If, in addition, operation is also conducted with an additional PCR on a surface, then this is either a solid-phase PCR of the type in which primers are additionally bound to the surface for the PCR step, or after the PCR, there is a purification step, preferably by means of a commercial purification kit (such as, for example, from the companies Promega or Qiagen) and subsequent binding of the PCR product to a surface onto which now the additional polymerase reaction for incorporating the labels will be conducted.

It is preferred that in the amplification, one of the primers is bound to a solid phase. For example, this solid phase can involve functionalized polymers, metals, glass or semiconductors such as silicon. The primers are bound preferably via bifunctional linker molecules, which are bound to a silanized surface or, for example, via thioates in the primer or thiol modifications to bromacetyl [acetyl bromide]-derivatized surfaces or gold.

In another, preferred alternative variant of the method, the incorporation of labels is produced also in a PCR reaction. In this case, the reaction occurs preferably without binding the primers to a solid phase. Instead, the PCR product is separated, for example, by gel electrophoresis, from other by-products and educts. The intensity of the signals emitted from the labels is determined by the bands or band patterns obtained and thus a conclusion is made of the degree of methylation in the fragment of sample DNA investigated.

If the complementary counterstrand to the treated DNA fragments is also produced in an amplification, then in the case of treatment with a bisulfite, in this counterstrand, adenine corresponds to an unmethylated cytosine position and guanine corresponds to a methylated cytosine position in the DNA sample. Therefore, it is also possible after amplification to conduct the method logically also with a labeled cytosine.

The primers used in the polymerase reactions most preferably do not amplify fragments of genomic DNA that is not treated with bisulfite (or only do so to a negligibly small extent), so that they are specific for the DNA converted with bisulfite. This protects from erroneous results in the case of an incomplete conversion reaction with sodium bisulfite, for example.

It is further preferred that the analysis is conducted by means of hybridization to oligomer arrays, wherein oligomers can be nucleic acids or molecules such as PNAs that are similar in their hybridization properties.

It is preferred that the methylation state of more than 10 methylation positions of the DNA to be analyzed is detected in one experiment.

It is also preferred according to the invention that the analysis is conducted by additionally measuring the length of the amplified DNA under investigation, whereby methods for length measurement comprise gel electrophoresis, capillary gel electrophoresis, chromatography (e.g. HPLC), mass spectrometry and other suitable methods. The fragments are thus detected via the labels incorporated in the polymerase reaction.

In addition, it is preferred that a conclusion is made on the presence of a disease or another medical condition of the patient from the methylation degree of individual or several different CpG islands investigated.

The labels are preferably introduced either by a label of the nucleotides during the polymerase reaction or amplification in the produced labeled fragments.

In addition, it is particularly advantageous that the labels are fluorescent labels or/and that the labels are radionuclides or/and that the labels are removable mass labels, which are detected in a mass spectrometer.

It is also preferred according to the invention that the fragments are detected overall in the mass spectrometer and are thus clearly characterized by their mass. Therefore, each incorporated label contributes a specific mass for the methylation, so that the number of methylations in the CpG island can be concluded from the measured molecular mass.

Another subject of the present invention is also the use of a method according to the invention for the diagnosis and/or prognosis of adverse events for patients or individuals, whereby these adverse events belong to at least one of the following categories: undesired drug effects; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as [a consequence of] an abnormality in the development process; malfunction, damage or disease of the skin, the muscles, the connective tissue or the bones; endocrine and metabolic malfunction, damage or disease; headaches or sexual malfunction.

The use of a method according to the invention is thus advantageous for distinguishing cell types or tissues or for investigating cell differentiation.

The subject of the present invention is also a kit comprised of a reagent containing bisulfite, primers for the polymerase reaction, as well as, optionally, instructions for conducting an assay according to the invention. A microtiter plate which possesses an activated surface for the immobilization of sample DNA and in which subsequent reaction steps also can be carried out is additionally a preferred component of this kit.

The method according to the invention consequently consists of the following steps:
a) DNA is extracted from a sample,
b) the DNA is treated, preferably with a bisulfite (=disulfite, hydrogen sulfite), in such a way that cytosine is converted into a base that is different in its base pairing behavior in the DNA duplex, while 5-methylcytosine remains unchanged,
c) one or more oligonucleotide primers are hybridized to the treated DNA,
d) the hybridized primers are extended in a polymerase reaction wherein labeled nucleotides are essentially incorporated only if cytosine bases were still present in the treated DNA after step b) and wherein the extent of the incorporation of labeled nucleotides correlates with the methylation in the DNA sample under investigation,
e) the labeled nucleotides that were not incorporated in the polymerase reaction are removed,
f) the number of labels in the fragment generated by primer extension is approximately determined by measuring the signal intensity emitted by these labels.

It is particularly preferred that the sample DNA is obtained from serum or other body fluids of an individual.

It is particularly preferred that the sample DNA is obtained from cell lines, blood, sputum, stool, urine, serum, cerebrospinal fluid, tissue embedded in paraffin, for example, tissue from eyes, intestine, kidney, brain, heart, prostate, lungs, breast or liver, histological slides and all possible combinations thereof.

It is also particularly preferred that the treatment according to claim 1b) is conducted with a bisulfite (=disulfite, hydrogen sulfite). It is also particularly preferred that the chemical treatment is conducted after embedding the DNA in agarose or most preferably after binding the DNA to a surface. In another particularly preferred method variant, in the chemical treatment, a reagent that denatures the DNA duplex and/or a radical trap is present.

It is also particularly preferred that genomic DNA is extracted from a sample and then is bound to a surface. It is also particularly preferred that this binding is produced by hybridization to an immobilized oligonucleotide. It is also preferred that the extracted DNA is cleaved by restriction enzymes prior to the binding.

In a particularly preferred conducting of the method, several different oligonucleotides are hybridized as primers to the treated DNA.

The labeled nucleotides are most preferably guanine derivatives, wherein these are essentially incorporated in the polymerase reaction, only if a cytosine methylation was present in the DNA sample at the corresponding positions. It is also preferred that the extent of incorporation of guanine bases and thus also the number of incorporated labels is proportional to the methylation in the DNA sample under investigation.

In a particularly preferred variant of the method, the polymerase reaction terminates preferably at the position which was cleaved by the use of a restriction endonuclease prior to the DNA isolation.

In another preferred method variant, the labeled nucleotides not incorporated in the polymerase reaction are removed by washing steps and the DNA is present bound to a surface.

The labels are, preferably, fluorescent labels, radionuclides, chemiluminescent labels or removable mass labels, which are detected in a mass spectrometer. It is also preferred that the labels are detected indirectly by the binding of an antibody labeled in a different way.

In another particularly preferred variant of the method, the treated DNA sample is amplified with the use preferably of at least two primer oligonucleotides, preferably by means of a polymerase chain reaction. In another particularly preferred method variant, the labeled nucleotides are cytosine derivatives, wherein these are essentially incorporated in the polymerase reaction, only if a cytosine methylation was present in the DNA sample at the corresponding positions.

A method in which the amplification of several fragments is conducted in one reaction vessel in the form of a multiplex-PCR is also preferred.

In another particularly preferred variant of the method, at least in one of the amplifications, one of the respective primers is bound to a solid phase.

The method according to one of the above, further characterized in that the amplificates are detected as a whole in the mass spectrometer and are thus clearly characterized by their mass.

The subject of the present invention is also the use of one of the described methods for the diagnosis and/or prognosis of adverse events for patients or individuals, whereby these adverse events belong to at least one of the following categories: undesired drug effects; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; malfunction, damage or disease of the respiratory system; lesion, inflammation, infection, immunity and/or convalescence; malfunction, damage or disease of the body as [a consequence of] an abnormality in the development process; malfunction, damage or disease of the skin, the muscles, the connective tissue or the bones; endocrine and metabolic malfunction, damage or disease; headaches or sexual malfunction.

The subject of the invention is also the use of a method according to one of the preceding claims for distinguishing cell types or tissues or for investigating cell differentiation.

SEQUENCE LISTING

<160> NUMBER OF SEQ ID NOS: 1

Figure 1:
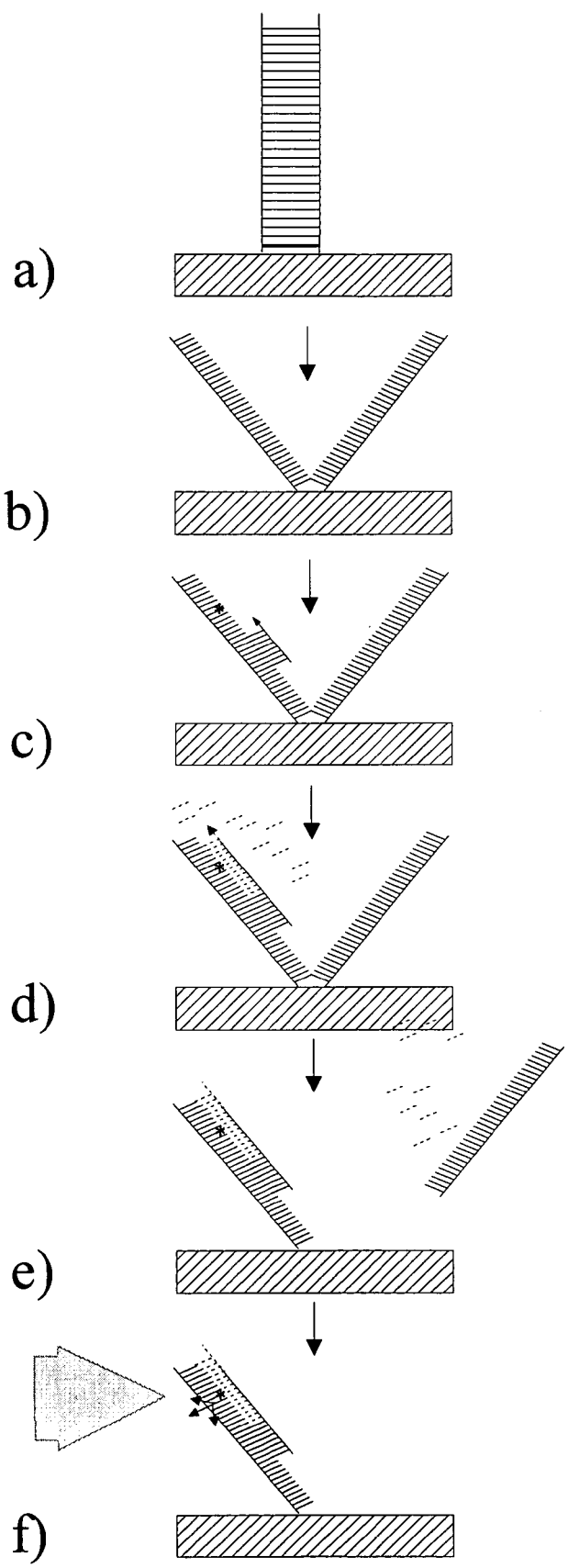
FIG. 1 illustrates a particularly preferred variant of the invention:
a) enzymatically cleaved sample DNA is bound to a surface and thus is separated from accompanying material
b) the DNA bound to the surface is denatured and then, for example, chemically treated with a bisulfite
c) a primer is bound to the DNA
d) an enzymatic primer extension reaction (nucleotides represented as dashed lines: - - - ) is conducted, and labels are incorporated only if cytosine methylations (*) were present previously in the sample DNA at the referred position.
e) the remaining labeled nucleotides and reaction components are removed in one washing step
f) the intensity of fluorescence emitted from the incorporated label is measured.

<210> SEQ ID NO 1
<211> LENGTH: 28
<212> TYPE: DNA
<213> ORGANISM: Homo Sapiens

<400> SEQUENCE: 1
gtttaggttt tttaggaagg agagagtg                                      28

The invention claimed is:

1. A method for the detection of cytosine methylation at more than 10 methylation positions within a CpG island in a DNA sample comprising:

a) extracting DNA from a sample,
b) binding the extracted DNA to a surface,
c) treating the bound DNA in such a way that cytosine is converted into a base that is different in its base pairing behavior in the DNA duplex, while 5-methylcytosine remains unchanged,
d) hybridizing one oligonucleotide primer to the treated DNA,
e) extending the hybridized primer by more than one nucleotide in a polymerase reaction to determine the methylation state at more than 10 methylation positions within a CpG island, wherein labeled guanine derivatives are essentially incorporated only if cytosine bases were still present in the DNA treated according to step c) and wherein the extent of the incorporation of labeled nucleotides correlates with the methylation of the CpG island in the DNA sample under investigation,
f) removing the labeled nucleotides that were not incorporated in the polymerase reaction,
g) determining approximately the number of labels in the fragment generated by primer extension by measuring the signal intensity emitted by these labels to determine the methylation state at more than 10 methylation positions, wherein the detection of more than 10 cytosine methylation positions within said CpG island in the DNA sample is afforded.

2. The method according to claim 1, further characterized in that the DNA samples are obtained from serum or other body fluids of an individual.

3. The method according to claim 1, further characterized in that the DNA samples are obtained from cell lines, blood, sputum, stool, urine, serum, cerebrospinal fluid, tissue embedded in paraffin, for example, tissue from eyes, intestine, kidney, brain, heart, prostate, lungs, breast or liver, histological slides and all possible combinations thereof.

4. The method according to claim 1, further characterized in that the treatment according to claim 1c) is conducted with a bisulfite.

5. The method according to claim 4, further characterized in that the chemical treatment is conducted after embedding the DNA in agarose.

6. The method according to claim 4, further characterized in that in the chemical treatment, a reagent that denatures the DNA duplex and/or a radical trap is present.

7. The method according to claim 1, wherein the binding of the extracted DNA to a surface comprises binding the DNA to an immobilized oligonucleotide by hybridization.

8. The method according to claim 1, further characterized in that the extracted DNA is cleaved by restriction enzymes prior to the binding.

9. The method according to claim 1, further characterized in that the polymerase reaction terminates preferably at the position which was cleaved by the use of a restriction endonuclease prior to the DNA isolation.

10. The method according to claim 1, further characterized in that the labeled nucleotides not incorporated in the polymerase reaction are removed by washing steps and the DNA is present bound to a surface.

11. The method according to claim 1, further characterized in that the labels are fluorescent labels, radionuclides, chemiluminescent labels or removable mass labels, which are detected in a mass spectrometer.

12. The method according to claim 1, further characterized in that the labels are indirectly detected by the binding of an antibody labeled in a different way.

13. The method according to claim 1, further characterized in that the amplificates are detected are a whole in a mass spectrometer and are thus clearly characterized by their mass.

14. The method according to claim 1, wherein said treating step comprises treating the DNA with a disulfite.

15. The method according to claim 1, wherein said treating step comprises treating the DNA with hydrogen sulfite.

16. A method for the diagnosis and/or prognosis of adverse events for patients or individuals, whereby these adverse events belong to at least one of the following categories: undesired drug effects; cancer diseases; CNS malfunctions, damage or disease; symptoms of aggression or behavioral disturbances; clinical, psychological and social consequences of brain damage; psychotic disturbances and personality disorders; dementia and/or associated syndromes; cardiovascular disease, malfunction and damage; malfunction, damage or disease of the gastrointestinal tract; damage or disease of the respiratory system; lesion, inflammation, infection, immunity and/or convalescence; malfunction, damage or disease of the body as an abnormality in the development process; malfunction, damage or disease of the skin, the muscles, the connective tissue or the bones; endocrine and metabolic malfunction, damage or disease; headaches or sexual malfunction, said method comprising:
  a) extracting DNA from a sample,
  b) binding the extracted DNA to a surface,
  c) treating the bound DNA in such a way that cytosine is converted into a base that is different in its base pairing behaviour in the DNA duplex, while 5-methylcytosine remains unchanged,
  d) hybridizing one oligonucleotide primer to the treated DNA,
  e) extending the hybridized primer by more than one nucleotide in a polymerase reaction to determine the methylation state at more than 10 methylation positions within a CpG island, wherein labelled guanine derivatives are essentially incorporated only if cytosine bases were still present in the DNA treated according to step c) and wherein the extent of the incorporation of labelled nucleotides correlates with the methylation of the CpG island in the DNA sample under investigation,
  f) removing the labelled nucleotides that were not incorporated in the polymerase reaction,
  g) determining approximately the number of labels in the fragment generated by primer extension by measuring the signal intensity emitted by these labels to determine the methylation state at more than 10 methylation positions, wherein the detection of more than 10 cytosine methylation positions within said CpG island in the DNA sample is afforded to diagnose or prognose said adverse events for patients or individuals.

17. A method for the differentiation of cell types or tissues or for the investigation of cell differentiation, said method comprising:
  a) extracting DNA from a sample,
  b) binding the extracted DNA to a surface,
  c) treating the bound DNA in such a way that cytosine is converted into a base that is different in its base pairing behaviour in the DNA duplex, while 5-methylcytosine remains unchanged,
  d) hybridizing one oligonucleotide primer to the treated DNA,
  e) extending the hybridized primer by more than one nucleotide in a polymerase reaction to determine the methylation state at more than 10 methylation positions within a CpG island, wherein labelled guanine derivatives are essentially incorporated only if cytosine bases were still present in the DNA treated according to step c) and wherein the extent of the incorporation of labelled nucleotides correlates with the methylation of the CpG island in the DNA sample under investigation,
  f) removing the labelled nucleotides that were not incorporated in the polymerase reaction,
  g) determining approximately the number of labels in the fragment generated by primer extension by measuring the signal intensity emitted by these labels to determine the methylation state at more than 10 methylation positions, wherein the detection of more than 10 cytosine methylation positions within said CpG island in the DNA sample is afforded to differentiate cell types or tissues or for the investigation of cell differentiation.

* * * * *